United States Patent [19]
Cox

[11] Patent Number: 5,860,942
[45] Date of Patent: Jan. 19, 1999

[54] DENTAL WATER IRRIGATOR EMPLOYING HYDRODYNAMIC CAVITATION

[76] Inventor: Dale W. Cox, 600 Lairport St., El Segundo, Calif. 90245

[21] Appl. No.: 815,517

[22] Filed: Mar. 12, 1997

[51] Int. Cl.[6] ........................................ A61L 17/02
[52] U.S. Cl. .................... 601/155; 601/160; 601/162; 601/169
[58] Field of Search .................... 601/154, 155, 601/159, 160, 162, 163, 165, 169

[56] References Cited

U.S. PATENT DOCUMENTS

| | | | |
|---|---|---|---|
| 3,542,017 | 11/1970 | Adams | 601/160 |
| 3,810,465 | 5/1974 | Lambert | 601/160 |
| 3,828,771 | 8/1974 | Gartner | 601/165 |
| 3,870,039 | 3/1975 | Moret et al. | 601/162 |

FOREIGN PATENT DOCUMENTS 1547821  3/1990  U.S.S.R. .................... 601/169

*Primary Examiner*—Danton D. DeMille
*Attorney, Agent, or Firm*—Allen A. Dicke, Jr.

[57] ABSTRACT

A handpiece has a cavitation orifice therein. A pump supplies water from a reservoir through the cavitation orifice to produce cavitation in the water downstream from the orifice. This cavitation produces OH radicals and ions in the water flow. The water flow is directed onto dental surfaces. The OH radicals and ions have been proven effective against bacterium.

20 Claims, 2 Drawing Sheets

DENTAL WATER IRRIGATOR EMPLOYING HYDRODYNAMIC CAVITATION

FIELD OF THE INVENTION

This invention is directed to a dental water irrigator employing hydrodynamic cavitation wherein the individual manipulates the hand piece of the irrigator to wash his teeth with cavitated water. The irrigator is configured to produce cavitation in the water stream and this cavitation produces chemical breakdown products which are effective against bacterium. Thus, this invention is directed to the new principle of applying hydrodynamic cavitation to deliver cavitation produced radicals and ions to dental surfaces for therapeutic purposes.

BACKGROUND OF THE INVENTION

Numerous attempts have been made to develop an apparatus to remove plaque or tartar from the surface of the teeth. Some of the previously developed apparatus includes the discharge of a water stream onto the teeth. Most of these devices suffer from lack of sufficient and effective power, such as caused by battery limitations. Several prior patents also claim their product produces "mild cavitations." This is an incorrect utilization of the technical term "cavitation."

The present invention uses hydrodynamic cavitation to produce therapeutic; radicals and ions in water to help eliminate and/or prevent periodontal diseases.

When a body of liquid is heated under constant pressure, or when its pressure is reduced at constant temperature by static or dynamic means, a state is reached at which vapor-filled micro-bubbles, become visible and grow. When vaporization is caused by heating, i.e. boiling, the change in state from liquid to vapor is slow because of the necessity to add heat, including the heat of vaporization. However, when the vapor is caused by quickly reducing the pressure on the liquid, such as expanding it through a nozzle, the vapor-filled micro-bubbles are rapidly formed.

The bubble growth is explosive because it is the result of vaporization to maintain conservation of energy. The condition is known as "cavitation" when it is caused by rapid pressure reduction at essentially constant temperature. Cavitation involves the entire sequence of events beginning with the bubble formation and extending through vapor bubble collapse.

In cavitated water, the heat from cavity implosion decomposes water into reactive hydrogen ions and hydroxyl radicals. Immediately following the breakdown, but at a slower rate, hydrogen ions and hydroxyl radicals recombine to form hydrogen peroxide and molecular hydrogen. Cavitation, thus, is a result of pressure reduction in the liquid and it can be controlled by controlling the amount of the pressure reduction. If the pressure is reduced and maintained for sufficient duration below a certain critical pressure (determined by the physical properties and initial pressure and temperature conditions of the liquid), it will produce cavitation.

Hydrodynamic cavitation is produced in this application when an aqueous solution at about 15 to 20 psig is forced through a nozzle into a vacuum of about 25" Hg. at the nozzle throat. A flow rate of approximately ⅛ gpm to ¼ gpm will produce the desired cavitation effect.

Several methods of adjusting the degree of cavitation and thus the amount of OH radical output are available.

1. Cavitation pump output pressure.
2. Change in the size of cavitation nozzle throat.
3. Change in the core angle of the diffusion throat.
4. Change in the length of the diffusion throat.
5. Change in the length of the focusing applicator.
6. Associated with methods of improving overall efficiency of the dental device would be adding cleansing or therapeutic solutions to the water tank. Such solutions might be diluted hydrogen peroxide and/or water soluble coenzyme CoQ10.

The phenomena of hydrodynamic cavitation has been demonstrated in many test series. For example, the following reports provide technical data and results in applications involving the removal of organic chemicals from aqueous solutions when the contaminants are in the ppb (parts per billion) range.

(1) EPA/540/AR-93/520: "CAV-OX® CAVITATION OXIDATION PROCESS."
(2) California Institute of Technology: Thesis "Ultrasonic Irradiation of Chemical Compounds in Aqueous Solutions."
(3) Science, 20 Sep. 19091, Vol. 253, pg. 1397.
(4) Scientific American, February 1989, pg. 80.

Further technical data can be found in Joseph Pisani U.S. Pat. Nos. 4,906,387 and 4,990,260 and in Dale W. Cox U.S. Pat. Nos. 5,326,468 and 5,494,585, the entire disclosures of which are incorporated herein by this reference.

SUMMARY OF THE INVENTION

In order to aid in the understanding of this invention, it can be said in essentially summary form that it is directed to a system for dental irrigation wherein hydrodynamic cavitation occurs sufficiently close to the point of water application to the teeth to deliver water breakdown products caused by cavitation to the dental surfaces for prophylaxis.

It is thus a purpose and advantage of the invention to be able to control the number of OH radicals produced and direct them against the teeth and gum lines where bacterium colonies thrive.

A further purpose and advantage of the invention is to provide a method of cleaning teeth on a daily basis that will essentially reduce and/or eliminate bacterium colonies from the teeth and gums.

A further purpose and advantage of the invention is to provide a dental cleaning device with a hydrodynamic cavitation nozzle, the output of which can be directed against the teeth and gums.

A further purpose and advantage of the invention is to provide a dental cleaning device with a hydrodynamic cavitation nozzle that can be changed to either a larger or smaller cavitation nozzle.

A further purpose and advantage of the invention is to provide a dental cleaning device with a hydrodynamic cavitation nozzle whose diffusion throat can be changed to provide selection of a longer or shorter throat.

A further purpose and advantage of the invention is to provide a dental cleaning device with a hydrodynamic cavitation nozzle and a diffusion throat, in which the diffusion throat can be lengthened or shortened, thereby controlling the residence time of the cavitation plume.

A further purpose and advantage of the invention is to provide a dental cleaning device with a hydrodynamic cavitation nozzle and a diffusion throat, in which the core angle of such diffusion throat can be removed and changed to a greater or smaller core angle, to enhance the efficiency of the output stream against bacterium colonies in the gums and teeth.

A further purpose and advantage of the invention is to provide a dental cleaning device with a hydrodynamic cavitation nozzle, a diffusion throat and a focusing applicator, the latter which can be lengthened or shortened, to direct the cavitated water against the gums and teeth, and therefore, against bacterium colonies residing thereon.

A further purpose and advantage of this invention is to provide a dental cleaning device with a hydrodynamic cavitation nozzle, a diffusion throat and a focusing applicator, with a water tank to which can be added small amounts of hydrogen peroxide, by which the overall cavitation process can be enhanced, thereby eliminating bacterium colonies in the gums and teeth.

A further purpose and advantage of the invention is to provide a dental cleaning device with a hydrodynamic cavitation nozzle, a diffusion throat and a focusing applicator, with a water tank to which can be added small amounts of water soluble CoQ10, a coenzyme that enhances the action of biological catalysts by which the overall cavitation process can be enhanced, thereby eliminating bacterium colonies in the gums and teeth.

Other purposes and advantages of this invention will become apparent from a study of the following portions of this specification, the claims and the attached drawings.

DESCRIPTION OF THE PREFERRED EMBODIMENT

Figure 1:
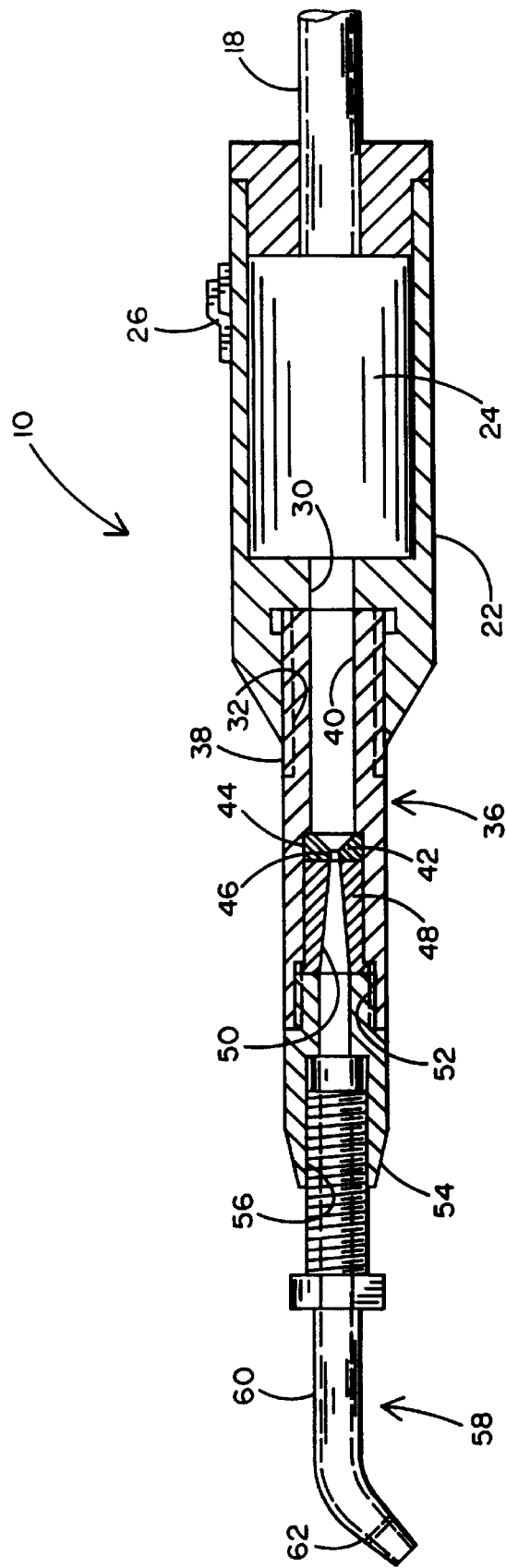
FIG. 1 is a view of the handpiece of the dental water irrigator of this invention, shown substantially in longitudinal section.
Figure 2:
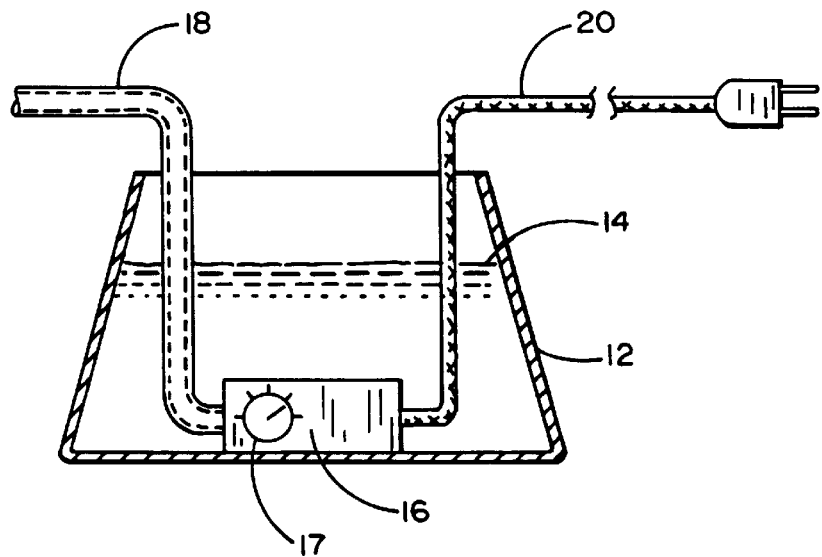
FIG. 2 is a section through the water reservoir showing the pressure pump therein for supplying water to the dental water irrigator of this invention.

FIG. 2 shows the source of water for the dental water irrigator 10 shown on FIG. 1. Reservoir 12 contains liquid 14 which is principally water. The liquid may contain small amounts of flavoring or small amounts of antibiotic or other therapeutic material, if desired. Pressure pump 16 is an electric multiple-stage rotary water pump which takes its suction from the reservoir 12 and delivers it out through supply tube 18. The pressure in supply tube 18, as a result of pump 16, is sufficient to cause cavitation in the liquid when the pressure on the liquid is rapidly reduced. The pressure in supply tube 18 is thus in the range of 20–25 psig. The pressure can be controlled by adjusting manual knob 17. Manual knob 17 may either control a relief valve which vents excess pressure back to the reservoir or may control pump motor speed. Electric line 20 supplies power to the motor connected to drive the pump in the pump/motor combination 16. The reservoir could be constructed with the primary pump/motor combination external thereto, such as below the liquid reservoir, if placement of the motor outside of the wet environment would be more desirable.

The dental water irrigator 10 in FIG. 1 has a frame 22 in which is positioned flow control reservoir 24. Switch 26 on frame 22 is also connected to control the electric motor in pump/motor combination 16. The switch 26 may be a multiple speed switch as well as an on/off switch. Supply tube 18 is connected to the reservoir inlet. The outlet of the reservoir 24 is an axial outlet passage 30 in frame 22. The outlet passage 30 enters into threaded recess 32 in the front of the frame 22. The pump 16 produces pressure in passage 30 in the range of 15 to 20 psig.

Figure 3:
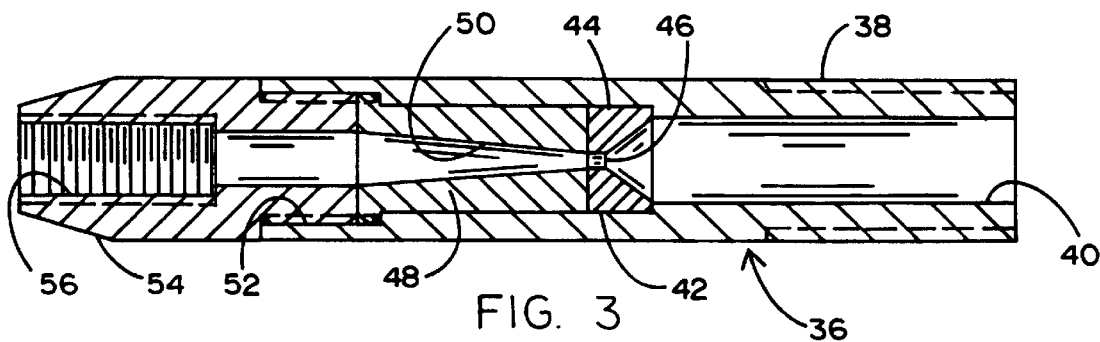
FIG. 3 is a longitudinal section through the body containing the cavitation orifice.

Cavitation body 36 is seen in FIGS. 1 and 3. It is preferably metallic. On its external surface, it has threads 38 which are sized to engage in the threaded recess 32 in frame 22. The cavitation body 36 is preferably a body of revolution having a longitudinal axis which lies on the central plane shown in section in FIGS. 1 and 3. Inlet passage 40 is in axial alignment with outlet passage 30 in frame 22. The inlet passage 40 terminates at shoulder 42. Orifice body 44 is a body of revolution and has an orifice 46 therein. Upstream of the orifice, the orifice body has an inlet cone which transitions between the inlet passage 40 and the orifice 46. Downstream from the cavitation orifice 46 is a diffusion body 48. The diffusion body 48 rests against orifice body 44. The interior of the diffusion body is a diverging surface in the downstream direction in the form of a cone having about a 12° total included angle. It is seen that the upstream cone in orifice body 44, the cylindrical cavitation orifice 46 and the conical downstream diffusion throat surface 50 in diffusion body 48 are surfaces which approximate the perfect hydrodynamic curves. However, for the purposes of this utilization, with the small size required, these approximations of the perfect hydrodynamic curves are sufficient. Furthermore, the orifice body and the diffusion body can be removed and replaced with similar bodies having different flow surface sizes and configurations to permit achieving the desired flow and cavitation conditions.

Figure 4:
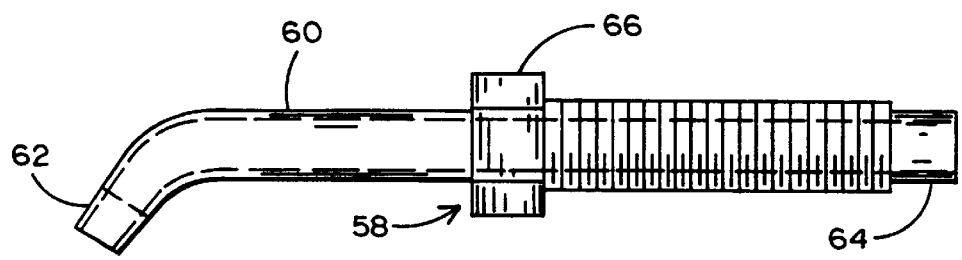
FIG. 4 is a side elevational view of the applicator nozzle with its collar taken in section.

The front of the cavitation body 36 has interior threads 52 into which is threaded nose 54. The nose retains the orifice body and the diffusion body in position within the cavitation body 36. Removal of the nose permits interchange of those parts. The nose 54 also has a threaded interior surface 56 to receive applicator 58, see FIG. 4. Applicator 58 comprises a tube 60 which has an outlet head 62 which is preferably angularly directed. As shown in dashed lines in FIG. 4, the applicator tube 60 has an open interior passage all the way therethrough and through the outlet head. The outlet head is preferably angular so that the liquid can be directed onto the desired tooth and gum surfaces. The inner end of tube 60 has a flange 64 thereon. Threaded collar 66 engages around the tube and against the flange. The threaded collar 66 threads into the interior threads 56 of nose 54. When the collar 66 is loosened, the tube 60 with its outlet head 62 can be rotatively adjusted but is not rotatable. With this construction the cavitation body can be readily changed to permit the use of different sizes and shapes of cavitation orifice and diffusion throat.

In normal operation of the system, pump 16 provides about 15 to 20 psig to inlet passage 40. The increase in velocity caused by the cavitation orifice 46 causes a sudden pressure reduction in the nozzle to about 25 inches of mercury, absolute. At the outlet end of the conical diffusion throat 50, the back pressure from applicator 58 is about 5 psig.

The pressurized water from the cavitation pump 16 is forced through nozzle orifice 46 causing abrupt reduction in pressure, causing hydrodynamic cavitation, causing the water to disassociate explosively into $OH^-$ radicals and $H^+$ ions. The micro-bubbles flow into the diffuser throat 50 and slowly collapse. The collapse of the micro-bubbles can cause very high instantaneous pressures and temperatures. When applied to environmental remediation applications, localized pressures of hundreds of atmospheres and temperatures as high as 5000° K at cavitation collapse have been reported in the literature. (Scientific American, February 1989) (Science, 20 Sep. 1991).

As the bubbles start to collapse, the free hydrogen forms hydrogen peroxide with the OH radicals. The OH radicals and the $H_2O_2$ flow out of applicator 58 of the device 10, and thence against the gums and teeth. Hydrodynamic cavitation, as applied to dental devices, will produce small, effective amounts of $OH^-$ and $H^+$ radicals combined with $H_2O_2$.

The length of the plume of radicals downstream from the cavitation nozzle in a dental device is estimated to be 2 to 3 inches. The time lapse from initiation in the throat to collapse of all micro-bubbles is estimated to be 0.1 second to 0.2 seconds. The micro-bubbles do not have a sufficiently long life so that they collapse on the tooth surface. This would be damaging to the tooth surface and is to be avoided. Instead, the flow rate is sufficient to bring the above-described radicals to the tooth surface. (These estimates are based in results from actual measurements in a 0.237" throat cavitation nozzle and scaled appropriately).

Several tests have been conducted using live cultures and hydrodynamic cavitation. Salmonella and *E. Coli* cultures were provided by Silliker Laboratories (a national testing laboratory). In a representative test with Salmonella, the culture was reduced from 2,300,000 CFU/ml to 6,600 CFU/ml, a 99.71% reduction. (Silliker Laboratories Report No. 88454.) It is believed that the bacteria in the human mouth will be similarly adversely affected as demonstrated in the above tests with Salmonella.

However, the cavitation nozzle in the dental irrigator 10 will be considerably smaller than in the above tested equipment, and thus, the production of $OH^-$ radicals will be less, so there will be little opportunity to cause deleterious problems in the gums themselves. Further, the amount of $OH^-$ radicals reaching the gums can be controlled in four ways: (1) the pump 16 output pressure, (2) changing the size of the cavitation orifice 44, (3) changing the length from the cavitation orifice 44 to the applicator outlet 62, and (4) changing the exit cone angle of diffusion throat 46.

This invention has been described and it is presently contemplated best embodiment, and it is clear that it is susceptible to numerous modifications, modes and embodiments within the ability of those skilled in the art and with the exercise of the inventive faculty. Accordingly, the scope of this invention is defined by the scope of the following claims.

What is claimed is:

1. A dental water irrigator comprising:
    a handpiece configured to be manually grasped and manipulated;
    means to supply a water containing liquid to said handpiece;
    means to pressurize the water so that water in said handpiece is pressurized to a sufficiently high pressure so that when it is passed through a cavitation nozzle cavitation and OH ions are produced in the water;
    a body in said handpiece, said body having a passage therethrough, said passage being connected to said means to pressurize water so that pressurized water is supplied through said passage;
    a convergent-divergent cavitation nozzle within said passage, said cavitation nozzle being sized and shaped to produce cavitation in said body in the continuous stream of water downstream from said nozzle sufficient to produce OH ions in the water downstream of said cavitation nozzle so that a continuous stream of water containing OH radicals and ions can be delivered to a dental surface.

2. The dental water irrigator of claim 1 further including a water reservoir between said means to pressurize water and said nozzle.

3. The dental water irrigator of claim 2 wherein said means to pressurize water comprises a motor-driven multi-stage rotary pump to raise the water pressure to said cavitation orifice to at least 15 psig.

4. The dental water irrigator of claim 3 wherein said reservoir has said rotary pump directly connected thereto.

5. The dental water irrigator of claim 4 further including an applicator on said handpiece, said applicator having an opening therethrough and being configured to deliver OH radical and ion containing water from said body to the dental surface.

6. The dental water irrigator of claim 5 wherein said applicator has an angular outlet head and said outlet head is adjustable as to direction to aid in delivering OH radical and ion-containing water to the dental surface.

7. The dental water irrigator of claim 2 further including an applicator on said handpiece, said applicator having an opening therethrough and being configured to deliver OH radical and ion containing water from said body to the dental surface.

8. The dental water irrigator of claim 7 wherein said applicator has an angular outlet head and said outlet head is adjustable as to direction to aid in delivering OH radical and ion-containing water to the dental surface.

9. The dental water irrigator of claim 1 further including an applicator on said handpiece, said applicator having an opening therethrough and being configured to deliver OH radical and ion-containing water from said body to the dental surface.

10. The dental water irrigator of claim 9 wherein said applicator has an angular outlet head and said outlet head is adjustable as to direction to aid in delivering OH radical and ion-containing water to the dental surface.

11. A dental water irrigator comprising:
    a handpiece;
    a reservoir for containing a liquid principally comprising water for delivery to a dental surface;
    means for delivering water containing liquid from said reservoir to said handpiece at a pressure sufficient to cause cavitation in the liquid when the liquid is passed through a cavitation nozzle;
    a body in said handpiece, said body having a passage therethrough connected to said means for delivering water, said passage including a convergent-divergent cavitation nozzle so that when water is supplied through said body and through said cavitation nozzle, water passing through said cavitation nozzle is cavitated in a continuous stream and produces OH radicals and ions in the continuous stream; and
    an applicator connected to said body for delivering a continuous stream of water containing cavitation-produced OH radicals and ions to the dental surface.

12. The dental water irrigator of claim 11 wherein said means for delivering water comprises a pump connected to said reservoir for delivering a continuous stream of water to said handpiece.

13. The dental water irrigator of claim 12 wherein said pump is configured to deliver water to said cavitation nozzle at sufficient pressure to cause cavitation in the water downstream from said cavitation nozzle.

14. The dental water irrigator of claim 11 wherein said reservoir has water, together with water soluble material selected from the group consisting of hydrogen peroxide and coenzyme CoQ10.

15. The dental water irrigator of claim 14 wherein said outlet head on said applicator is angular and is angularly adjustable for directing water containing cavitation produced OH radicals and ions onto a dental surface.

16. The dental water irrigator of claim 11 wherein there is an orifice body in said handpiece, said nozzle body having said cavitation orifice therein, said nozzle body being removable and exchangeable with respect to said handpiece.

17. The dental water irrigator of claim 16 wherein said convergent-divergent cavitation nozzle includes a convergent nozzle body and a separate diffusion body having a divergent surface which is divergent in the direction of flow so that cavitation in the continuous stream of water occurs and cavitation micro-bubbles collapse within said diffusion body.

18. The dental water irrigator of claim 11 wherein said convergent-divergent cavitation nozzle includes a convergent nozzle body and a separate diffusion body having a divergent surface which is divergent in the direction of flow so that cavitation in the continuous stream of water occurs and cavitation micro-bubbles collapse within said diffusion body.

19. The dental water irrigator of claim 18 wherein said diffusion body is separate from said cavitation body and is interchangeable therein.

20. The dental water irrigator of claim 19 wherein there is a nose piece engaged in said body, said nose piece engaging against said diffusion body to hold said diffusion body against said nozzle.

* * * * *